US008481755B2

(12) United States Patent
McArdle et al.

(10) Patent No.: US 8,481,755 B2
(45) Date of Patent: Jul. 9, 2013

(54) ACTIVATED METHYLENE REAGENTS AND CURABLE COMPOSITIONS PREPARED THEREFROM

(75) Inventors: Ciaran B. McArdle, Dublin (IE); Ligang Zhao, Duesseldorf (DE); Stefano Gherardi, Dublin (IE); Kevin Murnaghan, Dublin (IE)

(73) Assignee: Henkel Ireland Ltd., Monheim (DE)

( * ) Notice: Subject to any disclaimer, the term of this patent is extended or adjusted under 35 U.S.C. 154(b) by 361 days.

(21) Appl. No.: 12/766,015

(22) Filed: Apr. 23, 2010

(65) Prior Publication Data
US 2010/0199888 A1 Aug. 12, 2010

Related U.S. Application Data

(63) Continuation of application No. PCT/EP2008/064488, filed on Oct. 24, 2008.

(60) Provisional application No. 60/982,212, filed on Oct. 24, 2007.

(51) Int. Cl.
C07D 305/04 (2006.01)
C07C 291/10 (2006.01)

(52) U.S. Cl.
USPC .............................. 549/10; 558/302

(58) Field of Classification Search
USPC .............................. 549/10; 558/302
See application file for complete search history.

(56) References Cited

U.S. PATENT DOCUMENTS

| 2,363,464 A | 11/1944 | Senkus |
| 2,413,249 A | 12/1946 | Senkus |
| 2,413,250 A | 12/1946 | Senkus |
| 2,415,046 A | 1/1947 | Senkus |
| 2,582,128 A | 1/1952 | Hurwitz |
| 2,721,858 A | 10/1955 | Joyner et al. |
| 2,756,251 A | 7/1956 | Joyner et al. |
| 2,763,677 A | 9/1956 | Jeremias |
| 2,870,193 A | 1/1959 | Pollack et al. |
| 3,048,615 A | 8/1962 | Fields |
| 3,142,698 A | 7/1964 | Halpern et al. |
| 3,282,773 A | 11/1966 | Wicker |
| 3,554,987 A | 1/1971 | Smith |
| 3,903,055 A | 9/1975 | Buck |
| 3,975,422 A | 8/1976 | Buck |
| 3,988,299 A | 10/1976 | Malofsky |
| 3,995,641 A | 12/1976 | Kronenthal et al. |
| 4,003,942 A | 1/1977 | Buck |
| 4,012,402 A | 3/1977 | Buck |
| 4,013,703 A | 3/1977 | Buck |
| 4,056,543 A | 11/1977 | Ponticello |
| 4,160,864 A | 7/1979 | Ponticello |
| 4,202,920 A | 5/1980 | Renner et al. |
| 4,364,876 A | 12/1982 | Kimura et al. |
| 4,440,910 A | 4/1984 | O'Connor |
| 4,512,357 A | 4/1985 | Earl |
| 4,556,700 A | 12/1985 | Harris et al. |
| 4,560,723 A | 12/1985 | Millet |
| 4,587,059 A | 5/1986 | Harth et al. |
| 4,622,414 A | 11/1986 | McKervey |
| 4,636,539 A | 1/1987 | Harris et al. |
| 4,695,615 A | 9/1987 | Leonard et al. |
| 4,718,966 A | 1/1988 | Harris et al. |
| 4,764,545 A | 8/1988 | Yosida |
| 4,837,260 A | 6/1989 | Sato et al. |
| 4,855,461 A | 8/1989 | Harris |
| 4,876,045 A | 10/1989 | Longo et al. |
| 4,906,317 A | 3/1990 | Liu |
| 5,142,098 A | 8/1992 | Bru-Magniez et al. |
| 5,288,794 A | 2/1994 | Attarwala |
| 5,306,752 A | 4/1994 | Attarwala |
| 5,312,864 A | 5/1994 | Wenz et al. |
| 5,328,944 A | 7/1994 | Attarwala et al. |
| 5,340,873 A | 8/1994 | Mitry |
| 5,386,047 A | 1/1995 | Nakos et al. |
| 5,424,343 A | 6/1995 | Attarwala |
| 5,424,344 A | 6/1995 | Lewin |
| 5,455,369 A | 10/1995 | Meier et al. |
| 5,624,699 A | 4/1997 | Lang |
| 5,703,267 A | 12/1997 | Takahashi et al. |
| 5,744,642 A | 4/1998 | Lantzsch et al. |
| 5,994,464 A | 11/1999 | Ohsawa |
| 6,093,780 A | 7/2000 | Attarwala |
| 6,096,848 A | 8/2000 | Gololobov et al. |
| 6,174,919 B1 | 1/2001 | Hickey |
| 6,245,933 B1 | 6/2001 | Malofsky et al. |
| 6,291,544 B1 | 9/2001 | Kotzev |
| 6,531,460 B1 | 3/2003 | Takenouchi et al. |
| 6,833,196 B1 | 12/2004 | Wojciak |
| 6,835,789 B1 | 12/2004 | Kneafsey et al. |
| 2006/0094833 A1 | 5/2006 | McDonnell et al. |
| 2006/0269870 A1 | 11/2006 | Harada et al. |
| 2008/0241249 A1 | 10/2008 | Quintero et al. |

FOREIGN PATENT DOCUMENTS

CN 1837456 A 9/2006
DE 2 626 173 12/1977

(Continued)

OTHER PUBLICATIONS

Carl J. Buck, Unequivocal Synthesis of Bis(2-Cyanoacrylate) Monomers, I. VIa Anthracene Adducts, Journal of Polymer Science, Polymer Chemistry Edition, vol. 16, 2475-507 (1978).
G. Jones, "The Knoevenagle Condensation", Organic Reactions, vol. XV, 204, Wiley New York (1967).
F. Bigi et al., "Montmorillonite KSF as an Inorganic, Water Stable, and Reusable Catalyst for the Knoevenagel Synthesis of Coumarin-3-carboxylic Acids", Journal Organic Chemistry, vol. 64, 1033-35 (1999).
B. Green et al., Synthesis of Steroidal 16, 17-Fused Unsaturated δ-Lactones[1], Journal Organic Chemistry, vol. 50, 640-44 (1985).
P. Rao et al., "Zinc Chloride As a New Catalyst for Knoevenagel Condensation", Tetrahedron Letters, vol. 32, No. 41, 5821-22 (1991).
J. S. Yadav et al., "Phosphene-Catalyzed Knoevenagel Condensation: A Facile Synthesis of Cyanoacrylates and α-Cyanonitriles", European Journal Organic Chemistry, 546-51 (2004).
L. Tietze et al., Comprehensive Organic Synthesis, Pergamon Press, Oxford, vol. 2, Chapter 1.11, 341 (1991).
P. Laszlo, "Catalysis of Organic Reactions by Inorganic Sollds", Accounts of Chemical Research, vol. 19, 121-27 (1986).
K. Kloestra et al., "Base and Acid Catalysis by the Alkali-containing MCM-41 Mesoporous Molecul Sieve", Journal Chemical Soc. Chem. Commun., 1005-06 (1995).

(Continued)

Primary Examiner — Samantha Shterengarts
(74) Attorney, Agent, or Firm — Steven C. Bauman

(57) ABSTRACT

This invention relates to novel compounds with ester linkage(s) capped with either electron deficient olefinic linkage(s) or group(s) or reactive functional groups (termed herein as "active methylene reagents"), and curable compositions prepared therefrom.

1 Claim, 1 Drawing Sheet

FOREIGN PATENT DOCUMENTS

| | | |
|---|---|---|
| DE | 40 34 080 A1 | 6/1991 |
| DE | 19519958 | 12/1995 |
| EP | 0 127 855 | 12/1984 |
| EP | 0 267 981 A | 5/1988 |
| EP | 0 459 617 A1 | 12/1991 |
| GB | 2311519 A | 10/1997 |
| WO | WO 94/15590 A1 | 7/1994 |
| WO | WO 94/15907 | 7/1994 |
| WO | WO 95/32183 | 11/1995 |
| WO | WO 99/14206 A1 | 3/1999 |
| WO | WO 03/006225 A1 | 1/2003 |
| WO | WO 03/086605 A2 | 10/2003 |

OTHER PUBLICATIONS

P. Lednor et al., "The Use of a High Surface Area Silicon Oxynitride as a Solid, Basic Catalyst", *Journal Chemical Society, Chem. Commun.*, 1625-26 (1991).

F. Bigi et al., "A Revision of the Biginelli Reaction Under Solid Acid Catalysis. Solvent-free Synthesis of Dihydropyrimidines Over Montmorillonite KSF", *Tetrahedron Letters*, vol. 40, 3465-68 (1999).

F. Bigi et al., "Clean synthesis in water: uncatalysed preparation of ylidenemalononitriles"*Green Chemistry*, vol. 2, 101-03 (2000).

R. Breslow, "Hydrophobic Effects on Simple Organic Reactions in Water", *Accounts of Chemical Research*, vol. 24, 159-64 (1991).

C. Li, "Organic Reactions in Aqueous Media—With a Focus on Carbon-Carbon Bond Formation", *Chemical Reviews*, vol. 93, 2023-35 (1993).

T. Welton, "Room Temperature Ionic Liquids. Solvents for Synthesis and Catalysis", *Chemical Reviews*, vol. 99, 2071-83 (1999).

D. Morrison et al., "Base-promoted reactions in ionic liquid solvents. The Knoevenagel and Robinson annulation reactions", *Tetrahedron Letters*, vol. 42, 6053-55 (2001).

Fraga-Dubreiul et al., "Grafted ionic liquid-phase-supported synthesis of small organic molecules", *Tetrahedron Letter*, vol. 42, 6097-6100 (2001).

M. Smietana et al., "Preparation of Silyl Enol Ethers Using (Bistrimethylsilyl)acetamide in Ionic Liquids", *Organic Letters*, vol. 3, No. 7, 1037-39 (2001).

Li et al., "n-Butyl Pyridinium Nitrate as a Reusable Ionic Liquid Medium for Knoevenagel Condensation", *Chinese Chemical Letters*, vol. 14, No. 5, 448-50 (2003).

J. Harjani et al., "Lewis acidic ionic liquids for the synthesis of electrophilic alkenes via the Knoevenagel condensation", *Tetrahedron Letters*, vol. 43, 1127-30 (2002).

Xu et al., "Knoevenagel condensation Reaction Catalyzed by Functionalized Ionic Liquid 1-(2-Hydroxyethyl)-3-methyl Imidazolium Chloride", *Chinese Journal of Organic Chemistry*, vol. 24(10), 1253-56 (2004).

Su et al., "Organic Reactions in Ionic Liquids: Knoevenagel Condensation Catalyzed by Ethylenediammonium Diacetate", *Synthesis 2003*, No. 4, 555-59 (2003).

Moehrle et al., "Aminomethylierung von 1,3-Diketonen", *Pharmazie*, vol. 40, 697-701 (1985).

J. March, "Reactions", *Advanced Organic Chemistry*, 3$^{rd}$ Edition, Wiley & Sons Inc., 417 (1985).

J. March, "Addition to Carbon-Hetero Multiple Bonds", *Advanced Organic Chemistry*, 3$^{rd}$ Edition, Wiley & Sons, 802-03 (1985).

M. B. Smith, *Organic Synthesis*, McGraw Hill International Chemistry Series, 1302 (1994).

Tehrani et al., "Product Class 8: Iminium Salts", *Science of Synthesis*, vol. 27, 313-48 (2004).

B. Hin et al., "Facile Synthesis of α-Substituted Acrylate Esters", *Journal of Organic Chemistry*, vol. 67, 7365-68 (2002).

Holy et al., "The Mannich Reaction-II Derivatization of Aldehydes and Ketones Using Dimethyl(methylene)ammonium Salts", *Tetrahedron Letters*, vol. 35, 613-19 (1979).

Bryson et al., "Preformed Mannich Salts: A Facile Preparation of Dimethyl(methylene)ammonium Iodide", *Journal of Organic Chemistry*, vol. 45, 524-25 (1980).

J. March, "The Pinacol Rearrangement", *Advanced Organic Chemistry*, 3$^{rd}$ Edition, Wiley & Sons, 963-64 (1985).

J. March, "Free-Radical Substitution", *Advanced Organic Chemistry*, 3$^{rd}$ Edition, Wiley & Sons, 642 (1985).

Jahn et al., "A Novel and Simple Method for the Preparation of Iminium Salts", *Tetrahedron Letters*, vol. 34, No. 37, 5863-66 (1993).

R. J. Vijin et al., Synthesis, 573 (1994).

Davis, "Chemistry Letters", vol. 33, Issue 9, 1072-77 (2004).

Davis et al., "Ionic Liquids in Synthesis", P. Wasserscheid and T. Welton, eds., Wiley-VCH Verlag GmbH & Co. KGaA, Chapter 2 (2002).

M.G. Djamali, P. Burba, K.H. Lieser, "Snythese und Eigenschaften eines Celluloseaustauschers mit Diaminodibenzo-18-Krone-6 als Ankergruppe", *Die Angewandte Makromolecular Chemie*, vol. 92, 145-54 (1980).

K. Babic, "Reactive and Functional Polymers", vol. 66, 1494-1505 (2006).

Trumbo et al., "Copolymerization Behavior of 3-Isopropenyl-α,α-Dimethylbenzylamine and Preliminary Evaluation of the Copolymers in Thermoset Coatings", *Journal of Applied Polymer Science*, vol. 82, 1030-39 (2001).

T. Giesenberg et al., "Synthesis and Functionalization of a New Kind of Silica Particle." *Agnew. Chem. Int. Ed.*, 43, 5697-5700 (2004).

Zhang et al., "An Investigation of Knoevenagel condensation reaction in microreactors using a new zeolite catalyst", *Applied Catalysis A: General, 261*, 109-118 (2004).

Mehnert et al., "Chemical Communications", 3010 (2002).

Lee and Lee, "Bulletin of the Korean Chemical Society", vol. 25, Issue 10, 1531-37 (2004).

H. R. Snyder and W. E. Hamlin, "Alkylation of Nitroparaffins with Amines and Their Derivatives", *Journal of American Chemical Society*, vol. 72, 5082-85 (1950).

H. G. Johnson, "Reaction of Aliphatic Amines with Formaldehyde and Nitroparaffins. II. Secondary Amines", *Journal of American Chemical Society*, vol. 68, 12-14 (1946).

M. Semkus, "Journal of the American Chemical Society", vol. 68, 10-12 (1946).

Sarac, "Progress in Polymer Science", vol. 24, 1149-1201 (1999).

Brough et al., "Pyrimidinyl Nitronyl Nitroxides", *Chemical European Journal*, vol. 12, 5134 (2006).

Zhou et al., *J. Polym. Sci., Part A Polym. Chem. Ed.*, 29, 1097 (1991).

Mehrotra et al., "Journal of Organometalic Chemistry", vol. 24, 611-21 (1970).

Son et al., "Synthesis of Hexahydro-3,3,5,5,7-pentaalkyl-2H-1,4-diazepin-2-ones from 1,3-Diamines and Ketones", *J. Org. Chem.*, vol. 46, 323 (1981).

Senkus, Acetals of Nitro Alcohols and Corresponding Amino Acetals, *J. Amer. Chem. Soc.*, vol. 69, 1380-81 (1947).

Renner et al., "Cure of Epoxy Resins with Esters of Cyanoacrylic Acid", *Journal of Polymer Science: Polymer Chemistry Edition*, vol. 23, 2341 (1985).

Kennedy et al., "Macromers by Carbocationic Polymerization. X. Synthesis, Characterization, and Polymerizability of Cyanoacrylate-Capped Polyisobutylenes", *Journal of Macromolecular Science, Part A*, 28:2, 209-24 (1991).

Khrustalev et al., "Synthesis and X-ray structural study of 1-adamantylmethy 2-cyanoacrylatel and 1,10-decanediol bis-2-cyanoacrylate", *Russian Chemical Bulletin*, vol. 45, No. 9, 2172 (1996).

Y. Gololobov et al., "A novel approach to the synthesis of bis(2-cyanoacrylates)", *Russian Chemical Bulletin*, vol. 42, No. 5, 961 (1993).

Y. Gololobov et al., "Synthesis of bis(2-cyanoacrylates) from 2-cyanoacryloyl chloride and 2-butene-and 2-butyne-1,4-diols", *Russian Chemical Bulletin*, vol. 44, No. 4, 760 (1995).

J.-L. De Keyser et al., "A Versatile and Convenient Multigram Synthesis of Methylidenemalonic Acid Diesters", *J. Org. Chem.*, vol. 53, 4859 (1988).

Vijayalakshimi et al., "Alkyl and substituted alkyl 2-cyanoacrylates. Part I. Synthesis and Properties", *J. Adhesion Science Technology*, vol. 4, No. 9, 733 (1990).

Guseva et al., "Organic Chemistry. Synthesis of functionality substituted cyanoacetates." *Russian Chemical Bulletin*, vol. 42, No. 3, 478 (1993).

Guseva et al., "Organic Chemistry" *Russian Chemical Bulletin*, vol. 43, No. 4, 595 (1995).

Gololobov and Gruber, Russian Chemical Review, vol. 66, Issue 11, 953 (1997).

Senchenya et al., "Silicon-containing esters of α-cyanoacrylic acid: synthesis and properties" *Russian Chemical Bulletin*, vol. 42, No. 5, 909 (1993).

Bowie J. H. et al., "Tetrahedron", vol. 23, 305-20 (1967).

J. S. Norwick et al., J. Org. Chem., 57(28), 7364-66 (1992).

International Search Report for International Patent Application No. PCT/EP2008/064489 dated Dec. 30, 2008.

International Search Report for International Patent Application No. PCT/EP2008/064490 dated May 4, 2009.

International Search Report for International Patent Application No. PCT/EP2008/064488 dated Jul. 16, 2009.

H.C. Haas, et al., "Carbamylmethyl Esthers of Unsaturated Acids"; Journal of Polymer Science; vol. XXXVII, Issue 131; pp. 317-319; 1959, (XP002518680).

J.L. De Keyser et al., "A versatile and convenient multigram systhesis of methylidenamalonic acid diesters", J. Org. Chem., pp. 4859-48562, (1988) (XP002518681).

D.A. Aronovich, et al.; J. Appl. Chem. USSR.; vol. 52, pp. 900-902; 1979 (XP002518682).

X. Yang; Organic Preparations and Procedures International; vol. 30, No. 2; pp. 239-242; 1998 (XP002518684).

P.H. Mason, et al., "A New Route to Substituted Glutaric Acid Derivatives From Allylic Malonates"; Synthetic Communications; vol. 25(2); pp. 183-190; 1995.

M.L. Meketa, et al., "An Efficacious Method for the Halogenation of .beta.-dicarbonyl Compounds Under Mildly Acidic Conditions"; Tetrahedron Letter; vol. 46(28): pp. 4749-4751; 2005, XP002520970.

M.L. Meketa, et al., "An Efficacious Method for the Halogenation of .beta.-dicarbonly Compounds Under Mildly Acidic Conditions"; Tetrahedron Letter; vol. 46(28); pp. 4749-4751; 2005, XP002520971.

R.C. Cookson, et al., "2-Phenylthioallyl Alcohols and Their Use in the Synthesisi of 1,4-diketones and Cyclopentenones", Journal of Chemical Society, Chemical Communications; (23); p. 990; 1976, XP002520969.

P.H. Mason, et al., "Some Mechanistic and Synthetic Aspects of the DABCO Catalyzed Rearrangement of Allylic Esters"; Tetrahedron; vol. 50(41):pp. 12001-12008, XP002520967.

L.S. Boguslavskaya, et al., Journal of Organic Chemistry; vol. 9; pp. 295-299; 1793, XP002520972.

Vijayalakshimi, et al., "Synthesis and End Use Evaluation of Pinene-based Alicyclic Acrylates", *J. Polym. Mat.*, 13, pp. 127-131 (1996).

Yamada, et al., "Determination of Absolute Rate Constants for Radical Polymerization and Copolymerization of Ethyl a-Cyanoacrylate in the Presence of Effective Inhibitors against Anlonic Polymerization", Markromol. Chem., 184, 1025 (1983).

Vijayalakshimi, et al., "Synthesis of 3-Substituted-2-cyanoacrylates: Their Evaluation as Cross-link in Cyanoacrylate Adhesive Compositions", *J. Polym. Mat.*, 49, 1387 (1993).

Pines, Alul and Kolobieski, "Bromination of a-Methylstyrene with N-Bromosuccinimide, Snythes of 2-Phenly-1,5-hexadiene", *J. Org. Chem.*, 22, 1113 (1957).

T. Sato, et al., "Synthesis of Copper (II) Chelate of ethyl a-(acetoacetoxymethyl)acrylate and Its Radical-Initiated Polymerization"; Makromol. Chem., Rapid Commun. vol. 11; pp. 553-557; 1990.

M.L. Meketa, et al., "An Efficacious Method for the Halogenation of . beta.-dicarbonyl Compounds Under Mildly Acidic Conditions"; Tetrahedron Letter; vol. 46(28); pp. 4749-4751; 2005, XP002520970.

M.L. Meketa, et al., "An Efficacious Method for the Halogenation of .beta.-dicarbonyl Compounds Under Mildly Acidic Conditions"; Tetrahedron Letter; vol. 46(28); pp. 4749-4751; 2005, XP002520971.

R.C. Cookson, et al., "2-Phenylthioallyl Alcohols and Their Use in the Synthesisi of 1,4-diketones and Cyclopentenones"; Journal of Chemical Society, Chemical Communications; (23); p. 990; 1976, XP002520969.

P.H. Mason, et al., "Some Mechanistic and Synthetic Aspects of the DABCO Catalyzed Rearrangement of Allylic Esters"; Tetrahedron; vol. 50(41):pp. 12001-12008, XP002520967, 2008.

Samatha, et al., "Effect of Addition of Various Acrylates on the Performance of Ethyl Cyanoacrylate Adhesive", Polym.—Plast. Technol. Eng., 39(2), 381-92, (2000).

Vijayalakshmi, et al., "Synthesis and End Use Evaluation of Pinene-based Alicyclic Acrylates", *J. Polym. Mat.*, 13, pp. 127-131 (1996).

Yamada, et al., "Determination of Absolute Rate Constants for Radical Polymerization and Copolymerization of Ethyl a-Cyanoacrylate in the Presence of Effective Inhibitors against Anionic Polymerization", Makromol. Chem., 184, 1025 (1983).

Vijayalakshmi, et al., "Synthesis of 3-Substituted-2-cyanoacrylates: Their Evaluation as Cross-link in Cyanoacrylate Adhesive Compositions", *J. Polym. Mat.*, 49, 1387 (1993).

Ponticello, "The Preparation of a-Substituted Acrylic Esters", *J. Polym. Sci., Polym. Chem. Edn.*, 17, pp. 3509-3518 (1979).

Pines, Alul and Kolobieski, "Bromination of a-Methylstyrene with N-Bromosuccinimide, Snythes of 2-Pheny1-1,5-hexadiene", *J. Org. Chem.*, 22, 1113 (1957).

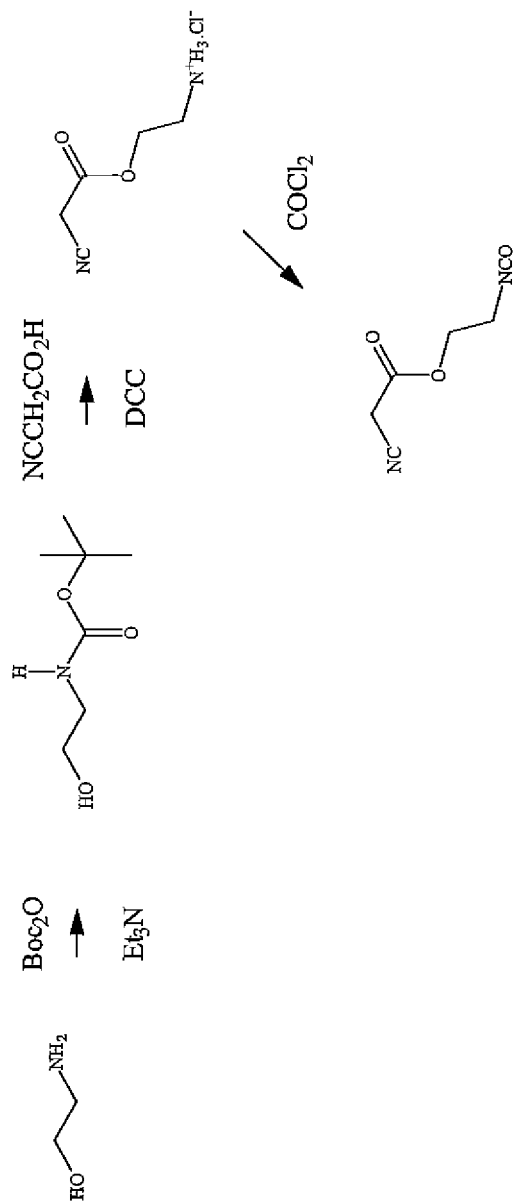

ACTIVATED METHYLENE REAGENTS AND CURABLE COMPOSITIONS PREPARED THEREFROM

BACKGROUND OF THE INVENTION

1. Field of the Invention

This invention relates to novel compounds with ester linkage(s) and either electron deficient olefinic linkage(s) or group(s) or reactive functional groups (termed herein as "active methylene reagents"), and curable compositions prepared therefrom.

2. Brief Description of Related Technology

Fast curing adhesives are well known. Most of those types of adhesives are based on cyanoacrylate chemistry.

Cyanoacrylate adhesives are known for their fast adhesion and ability to bond a wide variety of substrates. They are marketed as "super glue" type adhesives. They are useful as an all-purpose adhesive since they are a single component adhesive, very economical as only a small amount will do, and generally do not require any equipment to effectuate curing.

Traditionally, cyanoacrylate monomers have been produced by way of a Knoevenagel condensation reaction between a formaldehyde precursor, such as paraformaldehyde, and an alkyl cyanoacetate (an activated methylene reagent) with a basic catalyst. During the reaction, cyanoacrylate monomer forms and polymerises in situ to a prepolymer. The prepolymer is subsequently thermally cracked or depolymerised, yielding cyanoacrylate monomer. This approach has remained essentially the same over time, though various improvements and variants have been introduced. See e.g. U.S. Pat. Nos. 6,245,933, 5,624,699, 4,364,876, 2,721,858, 2,763,677 and 2,756,251.

In U.S. Pat. No. 3,142,698, the synthesis of difunctional cyanoacrylates using a Knoevenagel condensation reaction is described. However, the ability to thermally depolymerise the resulting, now crosslinked, prepolymer in a reliable and reproducible manner to produce pure difunctional monomers in high yields is questionable [see J. Buck, *J. Polym. Sci., Polym. Chem. Ed.*, 16, 2475-2507 (1978), and U.S. Pat. Nos. 3,975,422, 3,903,055, 4,003,942, 4,012,402, and 4,013,703].

A variety of other processes for producing cyanoacrylate monomers are known, some of which are described below. For instance, U.S. Pat. No. 5,703,267 defines a process for producing a 2-cyanoacrylic acid which comprises subjecting a 2-cyanoacrylate and an organic acid to a transesterification reaction.

U.S. Pat. No. 5,455,369 defines an improvement in a process for preparing methyl cyanoacrylate, in which methyl cyanoacetate is reacted with formaldehyde to form a polymer that is then depolymerised to the monomeric product, and in which the purity of yield is reported to be 96% or better. The improvement of the '369 patent is reported to be conducting the process in a poly(ethylene glycol) diacetate, dipropionate, or dibutyrate, having a number average molecular weight of 200-400, as the solvent.

U.S. Pat. No. 6,096,848 defines a process for the production of a biscyanoacrylate, which comprises the steps of esterifying a 2-cyanoacrylic acid or transesterifying an alkyl ester thereof to obtain a reaction mixture; and fractionally crystallizing the reaction mixture to obtain the biscyanoacrylate.

U.S. Pat. No. 4,587,059 defines a process for the preparation of monomeric 2-cyanoacrylates comprising the steps of (a) reacting (i) a 2,4-dicyanoglutarate with (ii) formaldehyde, cyclic or linear polymers of formaldehyde, or a mixture thereof, in the presence of between about 0.5 and about 5 mols of water per mol of 2,4-dicyanoglutarate, at an acid pH of about 3 to slightly less than 7, and at a temperature of about 70 to about 140, to form an oligomeric intermediate product, and (b) removing water that is present from step (a) and thermolyzing the oligomeric intermediate product for a period of time sufficient to effect its conversion to monomeric 2-cyanoacrylates.

Commercial production of cyanoacrylate monomers ordinarily relies on the depolymerisation of a prepolymer formed under Knoevenagel condensation reaction conditions, as noted above. Still today the Knoevenagel condensation reaction is believed to remain the most efficient and prevalent commercial method for producing high yields of monofunctional cyanoacrylates. Nevertheless, it would be desirable to not have to resort to thermally induced depolymerisation of a prepolymer produced by the Knoevenagel condensation reaction. This prospect may also enable facile access to highly useful difunctional monomers, such as so-called bis-cyanoacrylates or hybrid materials of cyanoacrylate and other polymerisable or reactive functionality.

Vijayalakshmi et al., *J. Ad. Sci. Technol.*, 4, 9, 733 (1990) describes some approaches to the synthesis of cyanoacetates and corresponding cyanoacrylates, including preparation from chloroacetic acid and its esters by subsequent reaction with sodium cyanide.

Guseva et al., *Russian Chem. Bull.*, 42, 3, 478 (1993) describes functionalized cyanoacetates, many of which were used in the subsequent synthesis of corresponding cyanoacrylates [Guseva et al., *Russian Chem. Bull.*, 43, 4, 595 (1994); see also Golobolov and Gruber, *Russian Chem. Rev.*, 66, 11, 953 (1997).]

One of the functionalized cyanoacetates noted in the preceding paragraph is glycidyl cyanoacetate. While the synthesis and characterisation of glycidyl cyanoacetate has been reported (such as is described in the preceding paragraph), the synthesis, characterisation and provision of performance characteristics of the corresponding glycidyl cyanoacrylate monomer have not to date been published. One explanation for this is that glycidyl cyanoacetate would not survive the conditions of a Knoevenagel reaction to make a cyanoacrylate monomer (initial base catalysis then subsequent exposure to high temperature in presence of strong acids) since epoxides are ring opened under such conditions. And while alternative routes to the glycidyl cyanoacrylate monomer may be conceivable, they would not employ glycidyl cyanoacetate at the outset.

Other cyanoacetates have been described, such as those with siliconised functionalities. See e.g. Senchenya et al., *Russian Chem. Bull.*, 42, 5, 909 (1993) and European Patent Document No. EP 0 459 617.

The preparation of mono-, di-, tri- and tetra-functional cyanoacetates as curatives for epoxy resins for adhesive applications has been described. Renner et al., "Cure of Epoxy Resins with Esters of Cyanoacrylic Acid", *J. Polym. Sci., Polym. Chem. Ed.*, 23, 2341 (1985) and U.S. Pat. Nos. 4,202,920 and 4,512,357.

Absent from the published literature, however, are activated methylene reagents, particularly those useful in the formation of electron deficient olefins and/or curable compositions prepared therefrom. Until now.

SUMMARY OF THE INVENTION

The present invention provides compounds within structure I:

I where A, B are each independently selected from H, $C_{1-4}$ alkyl, Li, Na, or K;
X is an electron withdrawing group, or Y;
Y is

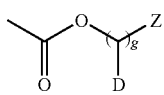

where D is selected from H, alkyl or aryl,
Z is either
(a)

where Q is
(i) an electron withdrawing group or
(ii) a first reactive functionality,
(b)

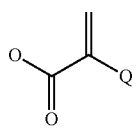

where Q is an electron withdrawing group, an alkyl group or an aryl group, or
(c) a second reactive functionality, and g is 1-12, desirably 1.

More specifically, the present invention provides compounds according to structure I that may be embraced by structure II

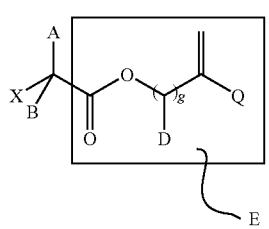

II where A and B are as defined above, X is an electron withdrawing group or E, E is as shown,

is a reactive functionality, where Q is defined herein, D is selected from H, alkyl or aryl, and g is 1-12, desirably 1.

Alternatively, the present invention provides compounds according to structure I that may be embraced by structure III

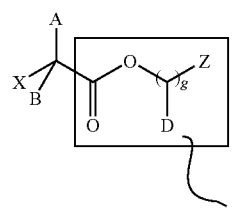

III where A and B are as defined above, X is an electron withdrawing group or F, D is selected from H, alkyl or aryl, Z is a reactive functionality, and g is 1-12, desirably 1.

Among other things, the novel compounds of the present invention are useful in the synthesis of electron deficient olefins, such as 2-cyanoacrylates.

The novel compounds are also useful as a constituent in the formulation of curable compositions together with imines, iminium salts, coreactants (as are illustrated below), cyanoacrylates or methylidene malonates, as is described herein.

BRIEF DESCRIPTION OF THE FIGURE

FIG. 1 depicts a synthetic scheme by which an active methylene compound according to the present invention may be prepared.

DETAILED DESCRIPTION OF THE INVENTION

As noted above, the present invention provides compounds within structure I:

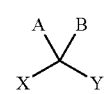

I where A, B are each independently selected from H, $C_{1-4}$ alkyl, Li, Na or K;
X is an electron withdrawing group, or Y;
Y is

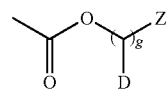

where D is selected from H, alkyl or aryl,
Z is either
(a)

where Q is
(i) an electron withdrawing group or
(ii) a first reactive functionality,
(b)

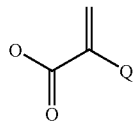

where Q is an electron withdrawing group, an alkyl group or an aryl group, or
(c) a second reactive functionality, and g is 1-12, desirably 1.

More specifically, as noted above X is an electron withdrawing group, which may be selected from CN, $CO_2R$, $CO_2H$, COCl, COR, $COPO(OR)_2$, $COPOR_2$, $SO_2R$, $SO_3R$ or $NO_2$, where R is $C_{1-4}$.

In addition, Y is

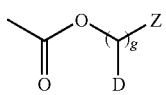

where D is selected from H, alkyl or aryl, Z is

where Q is an electron withdrawing group, which may be selected from CN, $CO_2R$, $CO_2H$, COCl, COR, $COPO(OR)_2$, $COPOR_2$, $SO_2R$, $SO_3R$ or $NO_2$, where R is $C_{1-4}$, and g is 1-12, desirably 1.

Alternatively, with reference to Y, Z is either (1)

where Q is a first reactive functionality selected from amides or thioamides, (2)

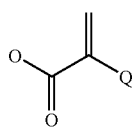

where Q is an electron withdrawing group, which may be selected from CN, $CO_2R$, $CO_2H$, COCl, COR, $COPO(OR)_2$, $COPOR_2$, $SO_2R$, $SO_3R$ or $NO_2$, where R is $C_{1-4}$, or an aryl group or substituted aryl group, or (3) a second reactive functionality, such as those selected from epoxides (such as cycloaliphatic epoxides), episulfides, oxetanes, thioxetanes, dioxolanes, dioxanes, isocyanates, maleimides, oxazolines, succinimides, 2-cyanoacrylates, methylidene malonates, acrylonitrile, (meth)acrylates, carboxylic acids and derivatives thereof, cyanoacetates, methylene malonates, hydroxyls, silanes, siloxanes, titanates, or zirconates.

However, structure I excludes allyl cyanoacetate, which is where A, B, D and Q (when defined as a reactive functionality) are each H and g is 1.

In addition, the present invention provides compounds embraced by structure IA

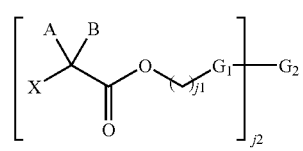

where A, B and X are as defined above, j1 is 1-12, $G_1$ is methylene, oxygen, sulfur, carbonyl or thiocarbonyl, $G_2$ is if j2 is 1 hydrogen, halogen (such as chlorine), hydroxyl, thiol, carboxylic acid or derivatives thereof, alkoxy or $T'(R')_f$, where T' is carbon, silicon, titanium, or zirconium, R' is hydrogen, alkyl, alkenyl, aryl, alkoxy, alkenyloxy, aryloxy, (meth)acryl, acrylamide, epoxide (such as cycloaliphatic epoxide), episulfide, oxetane, thioxetane, dioxolane, dioxane, isocyanate, or maleimide, and f is 3; or $G_2$ is if j2 is 2 alkylene, alkenylene, alkynylene, or arylene, with or without interruption by oxygen, sulfur, silicon and combinations thereof (such as siloxane), or $T'(R')_f$, where T' is carbon, silicon, titanium, or zirconium, R' is hydrogen, alkyl, alkenyl, aryl, alkoxy, alkenyloxy, aryloxy, (meth)acryl, acrylamide, epoxide (such as cycloaliphatic epoxide), episulfide, oxetane, thioxetane, dioxolane, dioxane, isocyanate, or maleimide, and f is 2; $G_2$ is if j2 is 4, carbon, silicon, oxygen carbon, oxygen silicon, oxygen titanium, or oxygen zirconium.

More specifically, compounds according to structure I may be embraced by structure II

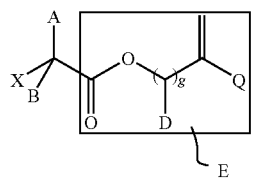

where A and B are as defined above, X is an electron withdrawing group or E, E is as shown,

is a reactive functionality, where Q is as defined herein, D is selected from H, alkyl or aryl, and g is 1-12, desirably 1.

Alternatively, compounds according to structure I may be embraced by structure III

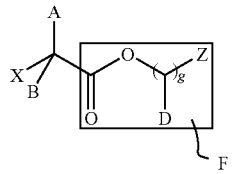
III where A and B are as defined above, X is an electron withdrawing group or F, D is selected from H, alkyl or aryl, Z is a reactive functionality, and g is 1-12, desirably 1. The reactive functionality of Z may be selected from epoxides, episulfides, oxetanes, thioxetanes, dioxolanes, dioxanes, isocyanates, maleimides, oxazolines, succinimides, 2-cyanoacrylates, methylidene malonates, acrylonitrile, (meth)acrylates, carboxylic acids and derivatives thereof, cyanoacetates, methylene malonates, hydroxyls, silanes, siloxanes, titanates, zirconates or

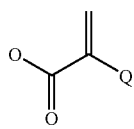

where Q is an electron withdrawing group, which may be selected from CN, $CO_2R$, $CO_2H$, COCl, COR, $COPO(OR)_2$, $COPOR_2$, $SO_2R$, $SO_3R$ or $NO_2$, where R is $C_{1-4}$. Alternatively Q may be hydrogen, an alkyl group (such as a methyl group) or an aryl group (such as a phenyl group or derivative thereof).

Representative examples of compounds within the scope of the invention include

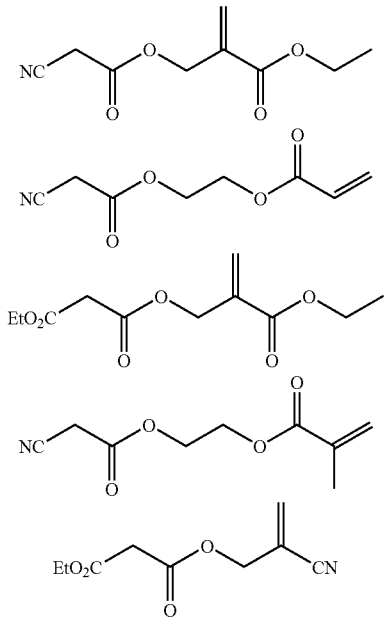

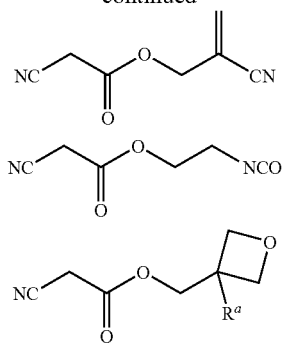

$R^a$ = methyl or ethyl

In addition, when compounds of structures II or III are polymerized or copolymerized, structures IIA or IIIA, respectively, may be realized

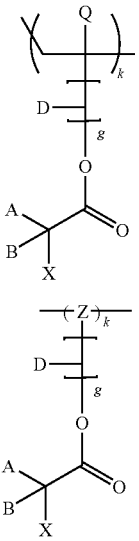
IIA

IIIA

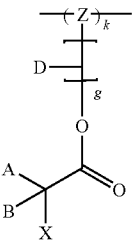

where A, B, X, D, Q and g are as defined herein, z is a reacted version or fragment of Z from above, and k is 2-100.

The present invention also provides compositions of the inventive compounds, together with a stabilizer package comprising at least one of a free radical stabilizer and an anionic stabilizer; and optionally, one or more additives selected from cure accelerators, thickeners, thixotropes, tougheners, thermal resistance-conferring agents, or plasticizers.

The cure accelerators that may be included with the inventive electron deficient olefins to form inventive compositions include calixarenes and oxacalixarenes, silacrowns, crown ethers, cyclodextrins, poly(ethyleneglycol) di(meth)acrylates, ethoxylated hydric compounds and combinations thereof.

Of the calixarenes and oxacalixarenes, many are known, and are reported in the patent literature. See e.g. U.S. Pat. Nos. 4,556,700, 4,622,414, 4,636,539, 4,695,615, 4,718,966, and 4,855,461, the disclosures of each of which are hereby expressly incorporated herein by reference.

For instance, as regards calixarenes, those within the following structure are useful herein:

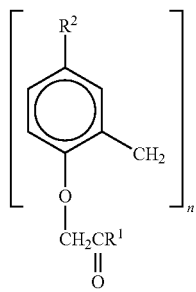

where in this connection $R^1$ is alkyl, alkoxy, substituted alkyl or substituted alkoxy; $R^2$ is H or alkyl; and n is 4, 6 or 8.

One particularly desirable calixarene is tetrabutyl tetra[2-ethoxy-2-oxoethoxy]calix-4-arene.

A host of crown ethers are known. For instance, examples which may be used herein include 15-crown-5, 18-crown-6, dibenzo-18-crown-6, benzo-15-crown-5-dibenzo-24-crown-8, dibenzo-30-crown-10, tribenzo-18-crown-6, asym-dibenzo-22-crown-6, dibenzo-14-crown-4, dicyclohexyl-18-crown-6, dicyclohexyl-24-crown-8, cyclohexyl-12-crown-4, 1,2-decalyl-15-crown-5, 1,2-naphtho-15-crown-5, 3,4,5-naphtyl-16-crown-5, 1,2-methyl-benzo-18-crown-6, 1,2-methylbenzo-5, 6-methylbenzo-18-crown-6, 1,2-t-butyl-18-crown-6, 1,2-vinylbenzo-15-crown-5, 1,2-vinylbenzo-18-crown-6, 1,2-t-butyl-cyclohexyl-18-crown-6, asym-dibenzo-22-crown-6 and 1,2-benzo-1,4-benzo-5-oxygen-20-crown-7. See U.S. Pat. No. 4,837,260 (Sato), the disclosure of which is hereby expressly incorporated here by reference.

Of the silacrowns, again many are known, and are reported in the literature. For instance, a typical silacrown may be represented within the following structure:

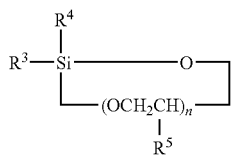

where in this connection $R^3$ and $R^4$ are organo groups which do not themselves cause polymerization of the cyanoacrylate monomer, $R^5$ is H or $CH_3$ and n is an integer of between 1 and 4. Examples of suitable $R^3$ and $R^4$ groups are R groups, alkoxy groups, such as methoxy, and aryloxy groups, such as phenoxy. The $R^3$ and $R^4$ groups may contain halogen or other substituents, an example being trifluoropropyl. However, groups not suitable as $R^4$ and $R^5$ groups are basic groups, such as amino, substituted amino and alkylamino.

Specific examples of silacrown compounds useful in the inventive compositions include:

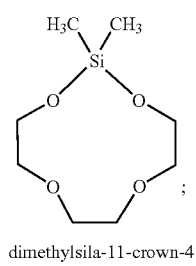

dimethylsila-11-crown-4

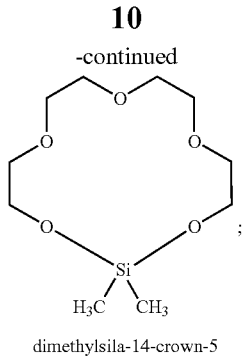

dimethylsila-14-crown-5

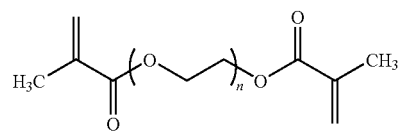

and dimethylsila-17-crown-6.

See e.g. U.S. Pat. No. 4,906,317 (Liu), the disclosure of which is hereby expressly incorporated herein by reference.

Many cyclodextrins may be used in connection with the present invention. For instance, those described and claimed in U.S. Pat. No. 5,312,864 (Wenz), the disclosure of which is hereby expressly incorporated herein by reference, as hydroxyl group derivatives of an α-, β- or γ-cyclodextrin which is at least partly soluble in the cyanoacrylate would be appropriate choices for use herein as the first accelerator component.

For instance, poly(ethylene glycol) di(meth)acrylates suitable for use herein include those within the following structure:

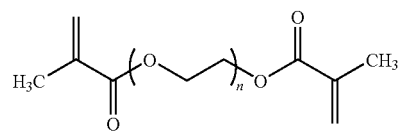

where n is greater than 3, such as within the range of 3 to 12, with n being 9 as particularly desirable. More specific examples include PEG 200 DMA (where n is about 4), PEG 400 DMA (where n is about 9), PEG 600 DMA (where n is about 14), and PEG 800 DMA (where n is about 19), where the number (e.g., 400) represents the average molecular weight of the glycol portion of the molecule, excluding the two methacrylate groups, expressed as grams/mole (i.e., 400 g/mol). A particularly desirable PEG DMA is PEG 400 DMA.

And of the ethoxylated hydric compounds (or ethoxylated fatty alcohols that may be employed), appropriate ones may be chosen from those within the following structure:

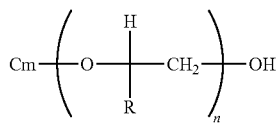

where $C_m$, can be a linear or branched alkyl or alkenyl chain, m is an integer between 1 to 30, such as from 5 to 20, n is an integer between 2 to 30, such as from 5 to 15, and R in this connection may be H or alkyl, such as $C_{1-6}$ alkyl.

Commercially available examples of materials within the above structure include those offered under the DEHYDOL tradename from Henkel KGaA, Dusseldorf, Germany, such as DEHYDOL 100.

When used, the cure accelerator should be included in the compositions in an amount within the range of from about 0.01% to about 10% by weight, with the range of about 0.1 to about 0.5% by weight being desirable, and about 0.4% by weight of the total composition being particularly desirable.

Other additives may be included with the inventive electron deficient olefins to form inventive compositions to confer additional physical properties, such as improved shock resistance, thickness (for instance, polymethyl methacrylate), thixotropy (for instance fumed silica), color, and enhanced resistance to thermal degradation [for instance, maleimide compounds such as N,N'-meta-phenylene bismaleimide (see U.S. Pat. No. 3,988,299 (Malofsky)), certain mono, poly or hetero aromatic compounds characterized by at least three substitutions on an aromatic ring thereof, two or more of which being electron withdrawing groups (see U.S. Pat. No. 5,288,794 (Attarwala)), certain quinoid compounds (see U.S. Pat. No. 5,306,752 (Attarwala)), certain sulfur-containing compounds, such as an anhydrosulfite, a sulfoxide, a sulfite, a sulfonate, a methanesulfonate or a p-toluenesulfonate (see U.S. Pat. No. 5,328,944 (Attarwala)), or certain sulfur-containing compounds, such as a sulfinate, a cyclic sultinate naphthosultone compound substituted with at least one strong electron withdrawing group at least as strongly electron withdrawing as nitro (see U.S. Pat. No. 5,424,343 (Attarwala)), and alkylating agents such as polyvinyl benzyl chloride, 4-nitrobenzyl chloride, and combinations thereof, silylating agents, and combinations thereof (see U.S. Pat. No. 6,093,780 (Attarwala)), the disclosures of each of which are hereby incorporated herein by reference. Such additives therefore may be selected from certain acidic materials (like citric acid), thixotropy or gelling agents, thickeners, dyes, thermal degradation resistance enhancers, and combinations thereof. See e.g. U.S. patent application Ser. No. 11/119,703 and U.S. Pat. Nos. 5,306,752, 5,424,344 and 6,835,789, the disclosures of each of which are hereby incorporated herein by reference.

These other additives may be used in the inventive compositions individually in an amount from about 0.05% to about 20%, such as about 1% to 15%, desirably 5% to 10% by weight, depending of course on the identity of the additive. For instance, and more specifically, citric acid may be used in the inventive compositions in an amount of 5 to 500 ppm, desirably 10 to 100 ppm.

Of course, the molecular design of the inventive compounds may render it less desirable to include one or more these additives with the inventive compounds to form inventive curable compositions.

The inventive compounds may be prepared by a process whose steps involve:

(a) providing a compound having at least two reactive groups (such as with reference to FIG. 1 an amino group and a hydroxyl group);

(b) contacting the compound having at least two reactive groups with an agent to block the reactivity of at least one of the groups to form a second compound having at least one remaining reactive group; and (c) reacting the second compound with an agent to convert the remaining reactive group to an electron withdrawing group and to remove the blocking group to yield a reactive group. The Examples section shows a more detailed illustration of this process.

The inventive compounds may be used to form electron deficient olefins or as a component in a curable composition. For instance, as regards the latter, the inventive compounds may be used in a curable composition that includes imines embraced by structure IV or iminium salts embraced by structure V.

The imine embraced within structure IV is as follows:

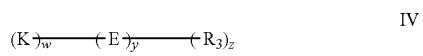
IV where K is

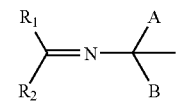

where in this connection $R_1$-$R_2$ are each independently selected from hydrogen, alkenyl, or alkynyl; and A-B are each independently selected from linear, branched, or cyclic alkyl or alkenyl which may be interrupted with heteroatoms or substituted by functional groups, or A and B taken together form a cyclic or polycyclic alkyl or alkenyl structure, which may be interrupted with heteroatoms or substituted by functional groups;

E is selected from a linear, branched or cyclic hydrocarbon with or without one or more nitrogen-containing substituents thereon, a heterocyclic, an aromatic or an organosiloxane group or part thereof or linkage; and $R_3$ in this connection is selected from a hydrocarbon, a heterocyclic, an aromatic or an organosiloxane group or linkage;

w is 1-100; y is 1-100 and z is 0-100.

When more than one of K, E or $R_3$ are present, each instance thereof is defined independently from the other instance(s).

The imine more specifically may be embraced within structure IVA as follows:

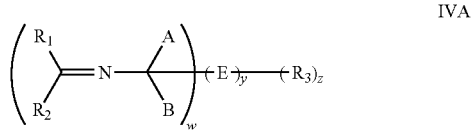
IVA where in this connection $R_1$-$R_2$, A-B, E, $R_3$, w, y and z are as defined above.

The iminium salt embraced within structure V is as follows:

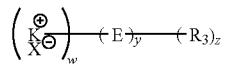

where K is

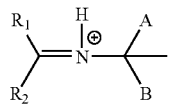

where in this connection $R_1$-$R_2$ are each independently selected from hydrogen, alkenyl, or alkynyl; and A-B are each independently selected from linear, branched, or cyclic alkyl or alkenyl which may be interrupted with heteroatoms or substituted by functional groups, or A and B taken together form a cyclic or polycyclic alkyl or alkenyl structure, which may be interrupted with heteroatoms or substituted by functional groups;

E is selected from a linear, branched or cyclic hydrocarbon with or without one or more nitrogen-containing substituents thereon, a heterocyclic, an aromatic or an organosiloxane group or part thereof or linkage; and $R_3$ in this connection is selected from a hydrocarbon, a heterocyclic, an aromatic or an organosiloxane group or linkage;

w is 1-100; y is 1-100 and z is 0-100; and

X is an anion.

When more than one of K, E or $R_3$ are present, each instance thereof is defined independently from the other instance(s).

The iminium salt may be embraced more specifically by structure VA as follows:

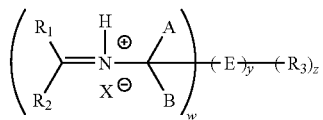

where in this connection $R_1$-$R_2$, A—B, E, $R_3$, w, y and z, and X are as defined above.

The imine in some cases may be an imine having an onium salt, such as an ammonium or amine salt functionality. In some cases the imines may be termed an "ionic liquid" (or "IL") or a task specific ionic liquid (or, "TSIL"), as will be discussed in more detail below. Likewise, the iminium salts may be termed an "ionic liquid" (or "IL") or a task specific ionic liquid (or, "TSIL"), as will be discussed in more detail below.

In such cases where the imine of structure IV or the iminium salt of structure V is particularly stable at room temperature conditions when in the presence of the inventive compounds, a modest amount of heat may be useful to allow the reaction to generate electron deficient olefins. Exposure to elevated temperature conditions is particularly desirable with iminium salts of structure V.

The inventive compounds may be used in a curable composition with the imine of structure IV or the iminium salt of structure V whose constituents also include:

(a) an imine within structure VI:

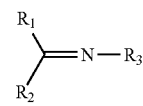

where $R_1$-$R_2$ are each independently selected from H, alkenyl, or alkynyl; and $R_3$ is a hydrocarbon moiety comprising a tertiary carbon which is attached to the N atom, where the tertiary carbon atom is attached to or part of one or more substituents selected from linear, branched, or cyclic, or one or more together form a cyclic or polycyclic (as the case may be) structure, which itself (themselves) may have substituents attached thereto.

The imines of structures IV or VI, or the iminium salt of structure V may be in the form of an IL having a melting point less than 100° C., which in its molten form contains only ions. The IL is also not distillable at a pressure of 1 mBar and a temperature of 100° C. The IL is in the liquid state at a temperature in the range of −10° C. to +250° C., such as in the range of 15° C. to +250° C., desirably in the range of 50° C. to +150° C.

The imine may be prepared from an aldehyde compound having the structure $R_1R_2C{=}O$, where $R_1$ is hydrogen and $R_2$ is a hydrogen, vinyl or propargyl. The aldehyde compound may be an aldehyde itself or a source of an aldehyde, such as one that yields an aldehyde like formaldehyde under appropriate reaction conditions. The aldehyde compound in a desirable embodiment includes formaldehyde (or a source thereof, such as paraformaldehyde, formalin, or 1,3,5-trioxane) or vinyl aldehydes, such as acrolein.

As a reactant with such an aldehyde is a primary amine. Primary amines attached to a carbon bearing no alpha protons are particularly desirable, such as t-alkyl primary amines. Rohm and Haas Co., Philadelphia, Pa. has sold commercially for a number of years a series of t-alkyl primary amines, which are designated as PRIMENE-brand amines.

For instance, t-alkyl primary amines available from Rohm and Haas include PRIMENE 81-R and PRIMENE JM-T. These PRIMENE-brand t-alkyl primary amines have highly branched alkyl chains in which the amino nitrogen atom is attached directly to a tertiary carbon. These t-alkyl primary amines consist of mixtures of isomeric amines, with PRIMENE 81-R consisting of an isomeric mixture with $C_{12}$-$C_{14}$ carbon branches and having an average molecular weight of 185 and PRIMENE JM-T consisting of an isomeric mixture with $C_{16}$-$C_{22}$ carbon branches and having average molecular weight of 269.

PRIMENE MD, also known as menthanediamine (1,8-diamino-p-menthane) or (4-amino-α, α-4-trimethyl-cyclohexanemethanamine, CAS No. 80-52-4), is a primary alicyclic diamine, in which both amino groups are attached to tertiary carbon atoms. Like other t-alkyl primary amines, menthanediamine is somewhat less reactive than similar straight chain diamines. Yet another PRIMENE, PRIMENE TOA has tertiary alkyl chains and a molecular weight of 129.

Versions of imine ammonium salts derived from PRIMENE MD (structure IX) after condensation with paraformaldehyde are shown below in structures X(a) and X(b). Such imine ammonium salts possess a structure, in which there exists an imine nitrogen attached to a tertiary carbon, and a quaternary ammonium salt in the same molecule. When X is methane sulfonate, for instance, the mixture of isomeric imine ammonium salts is liquidus at room temperature.

More specific examples of imines within structure VI are shown below, as structures XI-XVII.

IX
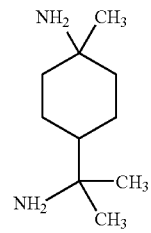

X(a)
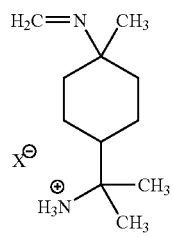

X(b)
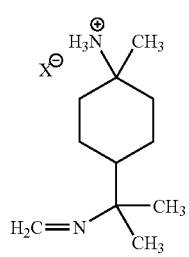

XI
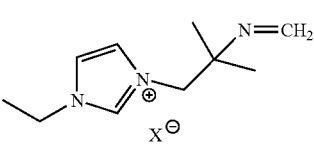

XII
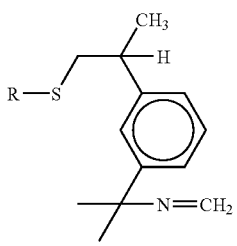

XIII
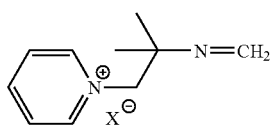

XIV
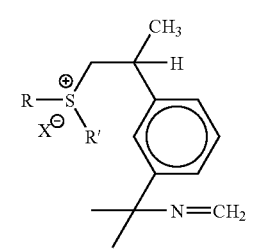

XV
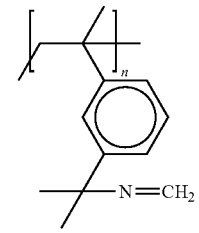

XVI
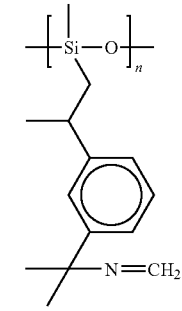

XVII
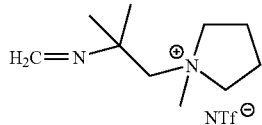

In the case of imines bearing an amine functionality as well, the amine functionality may be converted into ammonium salts, by contacting them with an acidic species, such as trifluoroacetic acid, acetic acid, sulphuric acid, methane sulfonic acid, benzene sulfonic acid and camphor sulfonic acid [see e.g. J. March at 802, and references cited therein; see also M. B. Smith, Organic Synthesis, McGraw Hill International, Chemistry Series, 1302 (1994) and references cited therein and Abbaspour Tehrani and De Kimpe, Science of Synthesis, 27, 313 (2004), and references cited therein]. When there is more than one basic functionality in the same molecule further mixtures may result, for example, in the above case, iminium salts may also form.

The imines, whether or not bearing ammonium salt functionality or whether or not they are tethered to a support, are then reacted with compounds of structure IV or V. In the compounds of structures IV and V, the electron withdrawing substituent is selected from nitrile, carboxylic acids, carboxylic esters, sulphonic acids, ketones or nitro.

Alternatively, or in addition, the inventive compounds may be used in a curable composition together with a coreactant. The coreactant may be selected from epoxides (such as cycloaliphatic epoxides), episulfides, oxetanes, thioxetanes, dioxolanes, dioxanes, isocyanates, maleimides, oxazolines, (meth)acrylates, acrylamides, cyanoacrylates, methylidene malonates, or vinyl ethers.

The present invention further provides curable compositions of the inventive compounds, together with a cyanoacrylate, a cyanopentadieneoate a methylidene malonate or combinations thereof.

For instance, the inventive compounds may be used in a curable composition that may include a cyanoacrylate within structure VII:

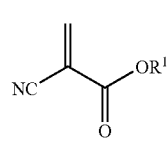

VII where $R^1$ in this connection is selected from $C_{1-16}$ alkyl, alkoxyalkyl, cycloalkyl, alkenyl, alkynyl, arylalkyl, aryl, allyl or haloalkyl groups. For instance, cyanoacrylate may be selected from methyl cyanoacrylate, ethyl-2-cyanoacrylate, propyl cyanoacrylates, butyl cyanoacrylates, octyl cyanoacrylates, allyl cyanoacrylate, β-methoxyethyl cyanoacrylate and combinations thereof.

Still alternatively, or in addition, the inventive compounds may be used in a curable composition that may include a methylidene malonate within structure VIII:

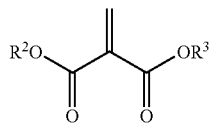

VIII where $R^2$ and $R^3$ in this connection are each independently selected from $C_{1-16}$ alkyl, alkoxyalkyl, cycloalkyl, alkenyl, alkynyl, arylalkyl, aryl, allyl or haloalkyl groups.

The following examples are intended to illustrate but in no way limit the present invention.

EXAMPLES

Example 1

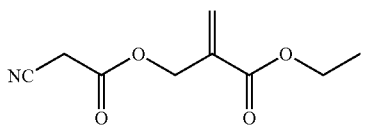

A

To a stirring mixture of cyanoacetic acid (90 g, 1.05 mol), ethyl 2-hydroxylmethyl acrylate (130 g, 1.0 mol), p-toluene sulfonic acid (500 mg) and hydroquinone (200 mg), was added toluene (150 mL), and the mixture was refluxed at a temperature of 150° C. to azeotropically remove water.

After cooling, the reaction product was washed consecutively with 30% brine and water. The organic layer was dried over anhydrous sodium sulfate, filtered and the solvent removed by rotary evaporator. The crude reaction product was purified by vacuum distillation (120-126° C./0.2 mbar), with the ester of structure A (102 g, 0.52 mol) isolated in a 52% yield. $^1$H NMR (60 MHz, CDCl$_3$): δ 6.39 (s, 1H), 5.89 (s, 1H), 4.90 (s, 2H), 4.28 (q, J=6.0 Hz, 2H), 3.50 (s, 2H), 1.32 (t, J=6.0 Hz, 3H); FT-IR (film): 2983.3, 2935.3, 2264.3, 1753.6, 1719.7, 1640.0, 1448.3, 1368.2, 1310.3, 1177.0, 1027.1, 817.2 cm$^{-1}$; GC/MS (EI) m/z (%): 198 (2) [M$^+$+H], 152 (40), 129 (25), 101 (38), 85 (100), 83 (45), 68 (80).

Example 2

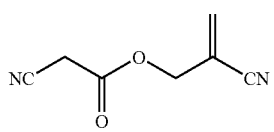

B

To a stirring solution of 2-hydroxymethylacrylonitrile (21 g, 0.25 mole) and cyanoacetic acid (20.5 g, 0.24 mole) in dry THF (0.5 l), was added a solution of dicarbodiimide ("DCC") (51.6 g, 0.25 mole) in dry THF (100 mL) over a period of time of 30 minutes at a temperature of 0° C. The reaction mixture was stirred overnight at room temperature and the solid material that formed was filtered off and washed with dry THF. The THF was removed in vacuo, the residue dissolved in dichloromethane and the solution passed through a pad of flash silica gel (200 g). The product obtained was purified additionally by precipitation with diethyl ether from its solution in dichloromethane furnishing 30.5 grams of the ester, B in a 81% yield. $^1$H NMR (250 MHz, CDCl$_3$): δ 3.58 (s, 2H), 4.80 (m, 2H), 6.13 (m, 1H), 6.19 (m, 1H); $^{13}$C NMR (62.9 MHz, CDCl$_3$): δ 24.4, 64.7, 112.6, 116.0, 116.8, 135.0, 162.4.

Example 3

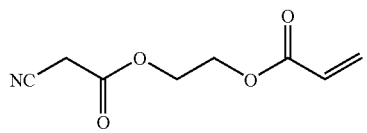

C

To a stirring mixture of cyanoacetic acid (42.5 g, 0.5 mol), 2-hydroxylethyl acrylate (81.2 g, 0.7 mol), conc. H$_2$SO$_4$ (3 drops) and hydroquinone (1.0 g), was added toluene (150 mL), and the mixture was refluxed at a temperature of 150° C. to azeotropically remove water.

After cooling, the reaction mixture was washed consecutively with 30% brine and water, and the organic layer was dried over anhydrous sodium sulfate, filtered and the solvent removed by rotary evaporator. The crude reaction product was purified by vacuum distillation (100-102° C./0.15 mbar), with the ester of structure C isolated. $^1$H NMR (60 MHz, CDCl$_3$): δ 6.59-5.84 (m, br, 3H), 4.37 (m, br, 4H), 3.78 (s, 2H); FT-IR (film): 2966.6, 2933.0, 2264.5, 1754.5, 1724.7, 1636.7, 1513.4, 1411.0, 1185.6, 1077.1, 984.1, 810.2 cm$^{-1}$.

Example 4

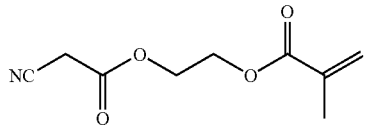

D

To a stirring mixture of cyanoacetic acid (42.5 g, 0.5 mol), 2-hydroxylethyl methylacrylate (65 g, 0.5 mol), PTSA (200 mg) and hydroquinone (1.0 g), was added toluene (200 ml) and the mixture was refluxed at a temperature of 150° C. to azeotropically remove water.

After cooling, the reaction mixture was washed consecutively with 30% brine and water, and the organic layer was dried over anhydrous sodium sulfate, filtered and the solvent removed by rotary evaporator. The crude reaction product could not be purified by vacuum distillation. $^1$H NMR (60 MHz, CDCl$_3$): δ 6.10 (s, 1H), 5.58 (s, 1H), 4.39 (b, 4H), 3.46 (s, 2H), 1.95 (s, 3H); FT-IR (film): 2962.8, 2931.2, 2264.6, 1753.4, 1719.4, 1637.3, 1452.9, 1320.3, 1163.4, 815.8 cm$^{-1}$; GC/MS (EI) m/z (%): 183 (2)[M$^+$+H], 112 (50), 69 (100), 41 (70).

Example 5

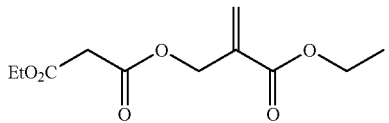

E

To a stirring mixture of monoethyl malonate (5.1 g, 38.6 mmol), ethyl 2-hydroxylmethyl acrylate (5.02 g, 3.86 mmol), PTSA (50 mg) and hydroquinone (50 mg), was added toluene (50 mL) and the mixture was refluxed at a temperature of 150° C. to azeotropically remove water.

After cooling, the reaction product was washed consecutively with 30% brine and water, and the organic layer was dried over anhydrous sodium sulfate, filtered and the solvent removed by rotary evaporator. The crude reaction product was purified by vacuum distillation (98-100° C./0.1 mbar) and the ester, E was isolated in 80% yield. $^1$H NMR (60 MHz, CDCl$_3$): δ 6.36 (s, 1H), 5.87 (s, 1H), 4.89 (s, 2H), 4.05-4.41 (m, 4H), 3.43 (s, 2H), 1.19-1.42 (m, 6H); FT-IR (film): 2984.7, 2908.6, 1735.3 (br), 1640.5, 1513.6, 1447.6, 1332.2, 1145.4, 1031.7, 817.2 cm$^{-1}$; GC/MS (EI) m/z (%): 245 (2) [M$^+$+H], 226 (2), 199 (20), 153 (20), 129 (70), 115 (100), 101 (40), 85 (45), 43 (65).

Example 6

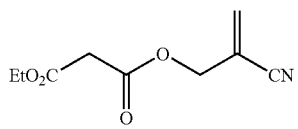

F

To a stirring mixture of monoethyl malonate (10.18 g, 77 mmol), ethyl 2-hydroxylmethyl acrylonitrile (7.67 g, 92 mmol), conc. H$_2$SO$_4$ (3 drops) and hydroquinone (1.0 g), was added toluene (50 mL) and the mixture was refluxed at a temperature of 150° C. to azeotropically remove water.

After cooling, the reaction product was washed consecutively with 30% brine and water, and the organic layer was dried over anhydrous sodium sulfate, filtered and the solvent removed by rotary evaporator. The crude reaction product was purified by vacuum distillation (86-88° C./0.05 mbar) and 7.5 g, 38 mmol of the ester, F was isolated in 49% yield. $^1$H NMR (60 MHz, CDCl$_3$): δ 6.10 (s, 2H), 4.75 (s, 2H), 4.20 (q, J=6.6 Hz, 2H), 3.47 (s, 2H), 1.34 (t, J=6.6 Hz, 3H); FT-IR (film): 3118.1, 2986.9, 2909.0, 2230.0, 1736.0, 1629.3, 1447.3, 1371.1, 1147.8, 1033.0, 959.6 cm$^{-1}$; GC/MS (EI) m/z (%): 197 (2) [M$^+$], 170 (40), 152 (100), 125 (10), 115 (50), 107 (15), 87 (25), 79 (45), 66 (90), 53 (40), 43 (60).

Example 7

Allyl cyanoacetate was prepared by direct esterification of cyanoacetic acid in the presence of methanesulfonic acid (85% after distillation). See Bowie, J. H. et al, *Tetrahedron*, 23, 305-320 (1967).

A solution of 3-chloroperoxybenxoic acid (100 g, tech. Grade 70-75% content) and allyl cyanoacetate (46 g, 0.37 mol) in chloroform was stirred under reflux with Dean-Stark trap for a period of time of 8 hours. Then the reaction mixture was cooled to a temperature of 0° C. and washed with a mixture of saturated NaHSO$_3$ and NaHCO$_3$ solutions (1:5) until the 3-chlorobenzoic acid by-product was removed (absence of peroxy acid was checked with starch-KI indicator). The organic fraction was separated and dried over MgSO$_4$, concentrated in vacuo, and distilled in a Kugelröhr apparatus at a temperature of 125° C. (in the oven)/0.01 torr furnishing 41 grams of cyanoacetic acid oxiranylmethyl ester in a 81% yield. $^1$H NMR (250 MHz, CDCl$_3$, ppm) 2.68 (dd, J$_{1,2}$=2.5, 5.0 Hz; 1H, CH$_2$), 2.88 (dd, J$_{1,2}$=4.2, 5.0 Hz; 1H, CH$_2$), 3.26 (m, 1H, CH), 3.55 (s, 2H, CH$_2$), 4.02 (dd, J$_{1,2}$=6.5, 12.0 Hz; 1H, CH$_2$), 4.56 (dd, J$_{1,2}$=2.7, 12.0 Hz; 1H, CH$_2$); $^{13}$C NMR (62.9 MHz, CDCl$_3$, ppm): 24.3, 44.2, 48.5, 66.7, 113.0, 162.9

Example 8

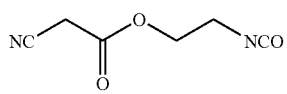

G

To a magnetically stirred solution of ethanolamine (40 g, 0.655 mol) and triethylamine (70 mL, 0.5 mol) in dichloromethane (1 L) was added molten di-tert-butylpyrocarbonate (110 g, 0.5 mol) over a period of time of 10 minutes while cooling with a water bath. After additional stirring for 2 hours the reaction mixture was washed with 1M HCl at a temperature of 0° C. to remove an excess of amines. Then the organic layer was washed with 10% NaHCO$_3$ and dried with MgSO$_4$. After removal of the solvent in vacuo the crude product was obtained as an oily liquid (78 g). This oil was dissolved in dry THF (1 L) and cyanoacetic acid (42.5 g, 0.5 mol) was added at 0° C. After complete dissolution, N,N'-dicyclohexylcarbodiimide ("DCC") (103.2 g, 0.5 mol) in dry THF (100 mL) was added over a 1-2 minute period of time. The reaction mixture was stirred overnight and the crystalline urea by-product was filtered off and washed with dry ether. The solvents were removed in vacuo and the residue was dissolved in dry ether and filtered once more. Into the filtrate was passed HCl gas to a concentration of 4-5 M to remove the Boc-protecting group. After stirring for 3 days a crystalline product was suction filtered giving the corresponding hydrochloride (53 g, 64% based on Boc₂O). ¹H NMR (250 MHz, DMSO-d⁶, ppm) 3.06 (m, 2H, CH₂), 4.08 (s, 2H, CH₂), 4.34 (t, J=5 Hz, 2H, CH₂), 8.35 (br, 3H, NH₃⁺).

To a stirred solution of that hydrochloride (53 g, 0.32 mol) in dry dichloromethane (1 L) pyridine (105 mL, 1.3 mol) was added at a temperature of 0° C. Then a phosgene solution (200 mL, ~2 M in toluene) was added while maintaining the reaction mixture below +10° C. See J. S. Norwick et al., *J. Org. Chem.*, 57(28), 7364-66 (1992). Stirring was continued for an additional period of time of 3 hours at an ice-bath temperature, at which point the mixture was washed with 2 M HCl, followed by a 10% aqueous solution of NaHCO₃, filtered through a 10 cm layer of packed MgSO₄, dried over anhydrous MgSO₄, filtered and evaporated to a residue. The residue was distilled twice using a Kugelröhr apparatus (175° C./0.001 torr) furnishing 35 grams of cyanoacetic acid 2-isocyanatoethyl ester, G in a 71% yield. ¹H NMR (250 MHz, CDCl₃, ppm) 3.53 (s, 2H, CH₂), 3.58 (t, J=6.5 Hz, 2H, CH₂), 4.31 (t, J=5.2 Hz, 2H, CH₂).

Example 9

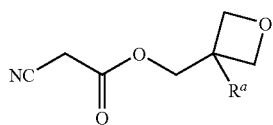

where $R^a$ is ethyl

To a solution of 3-ethyl-3-hydroxymethyl-oxetane (UBE Industries, 116.2 g, 1 mol) and ethyl-2-cyanoacetate (149 g, 1.3 mol) in a 500 mL one necked flask was added titanium (IV) butylate (Ti(O"Bu)₄, 0.7 g, 2 mmol). The mixture was refluxed for a period of time of 1.5 hours, and then distilled under a 10 mBar vacuum. The resulting orange residue was taken up in dichloromethane (200 mLs) and washed with deionised water (2×100 mLs). The organic layer was dried over sodium sulphate and distilled at a temperature of 150-155° C. and pressure of 0.2 mBar to furnish 92 grams of 3-ethyl-3-oxetanylmethyl-2-cyanoacetate, H1 in a yield of 50%. 60 MHz ¹H NMR (ppm, CDCl₃ containing 0.1% TMS internal standard) 4.42-4.35 (overlapped, 6H), 3.50 (2H), 1.72 (q) 2H, 0.93 (t) 3H; IR (cm⁻¹) 2965.2, 2877.1, 2261.9, 1744.3, 1460.0, 1397.4, 1336.6, 1259.7, 1178.4, 1004.3, 976.3, 826.9, 787.5, 739.7; GC-MS: 68 m/z, (100%), 41, 53, 57, 86.

Example 10

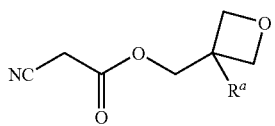

where $R^a$ is methyl

To a solution of 3-methyl-3-hydroxymethyl-oxetane (Aldrich Chemicals, 50 g, 0.49 mol) and ethyl-2-cyanoacetate (72 g, 0.64 mol) in a 500 mL one necked flask was added titanium (IV) butylate (Ti(O"Bu)₄, 0.4 g, 1.15 mmol). The mixture was refluxed for a period of time of 1.5 hours, and then distilled under a 10 mBar vacuum. The resulting orange residue was taken up in dichloromethane (200 mLs) and washed with deionised water (2×100 mLs). The organic layer was dried over sodium sulphate and distilled with the final fraction collected at a temperature of 100° C. and pressure of 0.17 mBar. The final fraction was collected in an amount of 38 g and a yield of 46%. The fraction was identified NMR, IR and GC-MS to be 3-methyl-3-oxetanylmethyl-2-cyanoacetate, H2. 60 MHz ¹H NMR (ppm, CDCl₃ containing 0.1% TMS internal standard) 4.42-4.25 (overlapped, 6H), 3.49 (s, 2H), 1.36 (s, 3H) IR (cm⁻¹) 2966.9, 2877.6, 2262.1, 1754.5, 1461.6, 1391.7, 1379.7, 1337.3, 1256.8, 1188.9, 1014.1, 977.1, 932.7, 834.4 GC-MS: 68 m/z (100%), 40, 57, 86.

What is claimed is:

1. Compounds having activated methylene groups for use in forming electron deficient olefins, the compounds selected from the group consisting of:

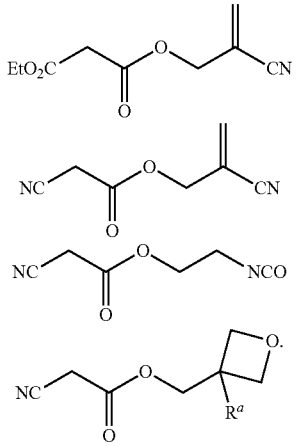

$R^a$ = methyl or ethyl

* * * * *